(12) United States Patent
Bitterman et al.

(10) Patent No.: US 9,029,350 B2
(45) Date of Patent: May 12, 2015

(54) METHODS OF USE OF BIOMATERIAL AND INJECTABLE IMPLANT CONTAINING BIOMATERIAL

(71) Applicant: Cutanea Life Sciences, Inc., Malvern, PA (US)

(72) Inventors: Robert J. Bitterman, Villanova, PA (US); Kimberley A. Forbes-McKean, Chester Springs, PA (US)

(73) Assignee: Cutanea Life Sciences, Inc., Wayne, PA (US)

(*) Notice: Subject to any disclaimer, the term of this patent is extended or adjusted under 35 U.S.C. 154(b) by 226 days.

(21) Appl. No.: 13/869,559

(22) Filed: Apr. 24, 2013

(65) Prior Publication Data

US 2013/0237498 A1    Sep. 12, 2013

Related U.S. Application Data

(60) Continuation of application No. 12/853,753, filed on Aug. 10, 2010, now Pat. No. 8,445,463, which is a division of application No. 11/677,319, filed on Feb. 21, 2007, now Pat. No. 7,776,840.

(51) Int. Cl.
 *A61K 31/722* (2006.01)
 *C08B 37/08* (2006.01)
 *A61K 31/197* (2006.01)
 *A61K 45/06* (2006.01)

(52) U.S. Cl.
 CPC .............. *A61K 31/722* (2013.01); *C08B 37/003* (2013.01); *A61K 31/197* (2013.01); *A61K 45/06* (2013.01)

(58) Field of Classification Search
 None
 See application file for complete search history.

(56) References Cited

U.S. PATENT DOCUMENTS

| | | | |
|---|---|---|---|
| 5,258,028 A | 11/1993 | Ersek et al. | |
| 5,451,406 A | 9/1995 | Lawin et al. | |
| 5,599,916 A | 2/1997 | Dutkiewicz et al. | |
| 5,658,593 A | 8/1997 | Orly et al. | |
| 5,731,298 A | 3/1998 | Reinmuller | |
| 6,214,331 B1 | 4/2001 | Vanderhoff et al. | |
| 6,413,526 B1 | 7/2002 | Bazin et al. | |
| 6,716,251 B1 | 4/2004 | Asius et al. | |
| 7,098,194 B2 | 8/2006 | Chenite et al. | |
| 7,316,822 B2 | 1/2008 | Binette et al. | |
| 7,511,023 B2 | 3/2009 | Kwon et al. | |
| 7,854,923 B2 | 12/2010 | Chen et al. | |
| 8,039,448 B2 | 10/2011 | Elson et al. | |
| 2003/0091851 A1 | 5/2003 | Khor et al. | |
| 2004/0092011 A1 | 5/2004 | Wilkison et al. | |
| 2004/0228886 A1 | 11/2004 | Ding et al. | |
| 2005/0106256 A1 | 5/2005 | Hung et al. | |
| 2005/0178396 A1 | 8/2005 | Hunter et al. | |
| 2005/0208122 A1 | 9/2005 | Allen et al. | |
| 2006/0173551 A1 | 8/2006 | Hubbard et al. | |
| 2006/0177480 A1 | 8/2006 | Sung et al. | |
| 2007/0077305 A1 | 4/2007 | Le et al. | |
| 2007/0202142 A1 | 8/2007 | Laugier et al. | |
| 2008/0008738 A1 | 1/2008 | Oliver et al. | |
| 2008/0107744 A1 | 5/2008 | Chu | |

FOREIGN PATENT DOCUMENTS

| | | |
|---|---|---|
| EP | 0251695 | 1/1988 |
| EP | 0648480 | 4/1995 |
| EP | 0711548 | 5/1996 |
| WO | 9633751 | 10/1996 |
| WO | 0187988 | 11/2001 |
| WO | 0240072 | 5/2002 |
| WO | 20040020473 | 3/2004 |
| WO | 20050105058 | 10/2005 |
| WO | 2006048829 | 5/2006 |
| WO | 2007096748 | 8/2007 |
| WO | 2008103594 | 8/2008 |

OTHER PUBLICATIONS

Aiedeh et al., "Synthesis of iron-crosslinked chitosan succinate and iron-crosslinked hydroxamated chitosan succinate and their in vitro evaluation as potential matrix materials for oral theophylline sustained-release beads" European Journal of Pharmaceutical Sciences (2001) vol. 13, pp. 159-168.
Remington: The Science and Practice of Pharmacy, edited by Alfonso R. Gennaro, Published 2000 by Lippincott Willams & Wilkins, pp. 745-747.
Silverman, The Organic Chemistry of Drug Design and Drug Action, published 1992 by Academic Press, pp. 4-47.
Sivakumar et al., "Preparation, characterizatoin, and in-vivo release of gentamicin from coralline hydroxyapatite-chitosan composite microspheres" Carbohydrate Polymers (2002) vol. 49, pp. 281-288.
"STN Database Descriptions", 2006 Chemical abstracts catalog, published 2006 by Chemical Abstracts Services, p. 52.
The Merck Manual of Diagnosis and Therapy, Seventeenth Edition, published 1999 by Merck Research Laboratories, pp. 407, 408, 459, and 460.

*Primary Examiner* — Eric Olson
(74) *Attorney, Agent, or Firm* — Greenberg Traurig LLP; Jonathan D. Ball

(57) ABSTRACT

This invention relates to the use of a biomaterial for the treatment, repair and/or enhancement of bodily tissue insufficiencies of the vocal chords, muscles, ligaments, cartilage, post-operative regions, sexual organs and/or weight supporting areas of the feet as well as other conditions of the bones and joints. The biomaterial for use in the invention may comprise an injectable bioresorbable polysaccharide composition wherein the polysaccharide may be succinochitosan glutamate. This invention also relates to the use of a biomaterial comprising an injectable bioresorbable polysaccharide composition in which resorbable particles may be in suspension, the said particles comprising or consisting essentially of chitin and/or chitosan, which may be free of any additional formulation modifying agents, and a process for manufacturing the same. The invention also includes the use of various medicaments in the biomaterial formulations to enhance the treatment of the affected area of the body.

16 Claims, 1 Drawing Sheet

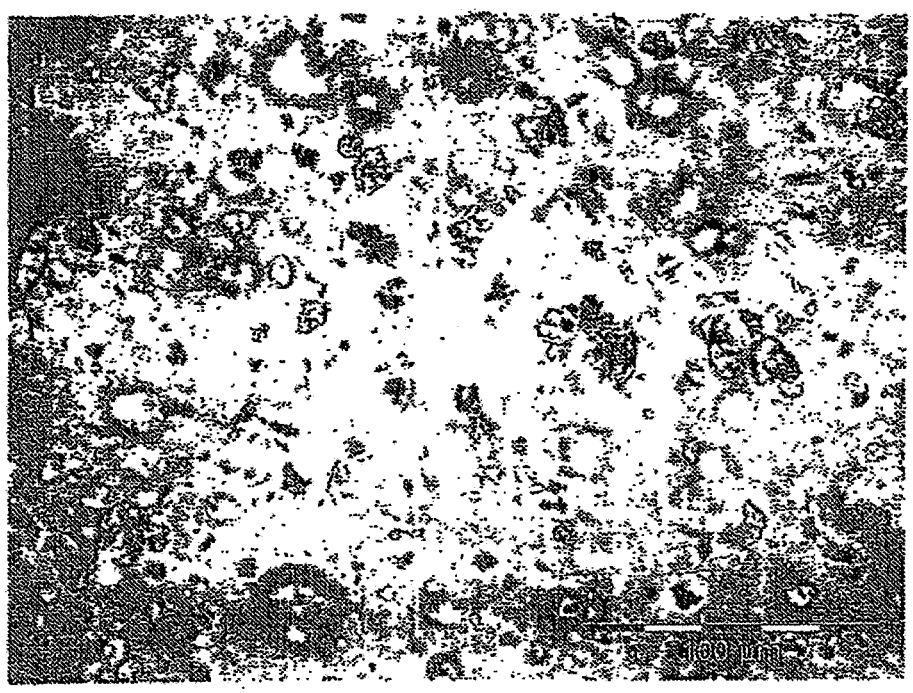

METHODS OF USE OF BIOMATERIAL AND INJECTABLE IMPLANT CONTAINING BIOMATERIAL

This application is a continuation of U.S. application Ser. No. 12/853,753, filed Aug. 10, 2010, which is a divisional of U.S. application Ser. No. 11/677,319, filed Feb. 21, 2007, the contents of which are hereby incorporated by reference in their entirety.

FIELD OF INVENTION

The present invention relates to the field of biomaterials for implantation in the human or animal body. More particularly, the present invention relates to methods of use of an implantable biomaterial, which may comprise chitin and/or chitosan. The biomaterial of this invention may be in the form of a gel, and may be injected, in particular by the subcutaneous or intradermal route, to form an implant. This implant has the benefit of being bioresorbable.

BACKGROUND OF INVENTION

Experts in the field are familiar with various injectable implants. For example, silicon gels (or silicon oils) are well-known, but these gels have the inconvenience of not being biodegradable. Moreover, silicon is often the cause of chronic inflammation, granuloma formation and even delayed allergic reactions. Collagen suspensions have also been very widely used over the past ten years. However, collagen generally is of bovine origin, which is undesirable for health and generally subject to additional regulatory requirements. Attempts to re-implant fatty cells removed from the patients themselves are also reported. However, the duration of the filling effect is generally less than the patient would like.

Other implants have been used, comprising a gelatine or collagen solution including, in suspension, polymethyl methacrylate (PMMA) microspheres having a diameter of 20 to 40 μm. PMMA, however, is not biodegradable and the gelatine or collagen solution is generally derived from bovine sources.

EP 0 969 883 describes an implantable gel including L-PLA (polylactic acid) microspheres with a diameter of 20 to 40 μm suspended in a carboxy methylcellulose gel (CMC). This gel is injectable and can be supplied in a sterile syringe. This product shows an acceptable efficacy but may present poor syringability (clogging of the required low-diameter needles may be noted) and a biodegradability which is too slow for some of the desired applications. The particles have the tendency to aggregate in the packaging, in particular in a syringe, making injections difficult and leading to inconsistent results. Non-homogeneous distribution of the particles in the injection area may actually be observed in patients. The expected aesthetic result is therefore not achieved and areas overloaded with particles are noted, sometimes adjacent to areas free of particles. The very long resorption time of the PLA (having a high molecular weight) may be of several years, which may also lead to inflammatory reactions in the long run.

There are numerous novel applications for biomaterials which do not have the disadvantages of the prior art materials, and particularly methods of using biomaterials which are useful as immediate filler materials, able to generate fibrosis and also capable of being resorbed to avoid chronic inflammatory reactions or rejection in the long run.

SUMMARY OF INVENTION

The present invention is directed to several new uses of biomaterials including for the treatment, repair and/or enhancement of bodily tissue insufficiencies of the vocal chords, muscles, ligaments, cartilage, post-operative regions, sexual organs and/or weight supporting areas of the feet as well as other conditions of the bones and joints. The biomaterials which may be used in the invention may comprise an injectable composition, preferably in the form of a gel of chitin or chitosan, such as for example a succinochitosan glutamate gel, preferably including particles in suspension in the composition, said particles comprising chitin and/or chitosan. The biomaterial of the invention is bioresorbable, and when particles are in suspension they are bioresorbable, as well. The resorption time of the gel may be different from the resorption time of the particles. Various medicaments may also be used to enhance the treatment of the affected area of the body.

According to the invention, the use of the biomaterial of the invention produces a filling effect, resulting from the injected volume of composition. An important goal of the biomaterial for use in the invention is to induce fibrosis and tissue formation.

DESCRIPTION OF FIGURES

FIG. 1 is a photo showing the distribution of chitin particles for a succinochitosan glutamate gel containing 1% chitin particles. The photo of the biomaterial, taken using an OLYMPUS® optical microscope, confirms that the particles are distributed homogeneously throughout the gel, naturally remaining in suspension due to the surfactant properties of chitosan, without the need of additional surfactants.

DETAILED DESCRIPTION OF THE INVENTION

Injecting a high amount of the biomaterial of the invention in a single injection may not be the optimal method of treating patients in need of said biomaterial, since the enhancement of the tissue (e.g., dermis) may not depend on the amount of biomaterial injected in a single injection; it may be preferred to carry out several injections, which may be distant of a few weeks, for example two months. This embodiment aims at letting the biomaterial almost totally resorb before injecting new biomaterial.

Fibrosis is induced by biomaterial, which means by the composition and by the particles present in the biomaterial of the invention. When the biomaterial is injected, it is perceived as foreign bodies and the body responds to this attack by connective tissue hyperplasia, with proliferation of fibroblasts developing from collagen (neo-collagenesis). Fibrosis reaction induced by injecting the biomaterial of the invention may occur between 15 days and 3 weeks after injection.

Inducing fibrosis by injecting the biomaterial, is aimed to create natural filling tissue which will replace the biomaterial when it is resorbed. It is therefore desirable that the particles, which may be considered as being principally responsible for inducing the fibrosis, be resorbed once they no longer fulfill their function of inducing fibrosis, preferably within a period of 1 to 6 months.

Thus, the biomaterial to be used according to the invention, partly because of the nature of its composition and partly because of the presence of particles, proposes a technical solution for patients in need for implantable filling material, and the product biodegradation and resorption time of the biomaterial may be adapted to the specific needs of the patients, for example by adjusting the amount of particles in the composition, thus avoiding the drawbacks of the prior art products.

In the present invention, by syringability is meant the ease of injection of the biomaterial; syringability generally may be a function of viscosity and other rheological properties of the biomaterial and of the size of the particles included within the biomaterial and of diameter of the needle of the syringe. By chitin, is meant a linear polysaccharide of beta-1.4-N-acetyl-D-glucosamine. By chitosan is meant a linear polysaccharide composed of randomly distributed linked beta-1.4-linked N-acetyl-D-glucosamine (acetylated unit) and D-glucosamine (deacetylated unit). The degree of deacetylation of chitosan may be determined by NMR spectroscopy.

By chitosan derivative, is meant any chitosan salt or acid-derived chitosan, chitosan glycolate, chitosan lactate, chitosan succinate, hydroxyalkyl chitosan, chitosan acetate, chitosan glutamate and more preferably succinochitosan glutamate.

According to a preferred embodiment of the invention, the biomaterial to be used according to the invention comprises or consists of an injectable bioresorbable polysaccharide composition, preferably in the form of a gel, including resorbable particles in suspension within the composition, said particles comprising chitin and/or chitosan.

In one embodiment, the polysaccharide is chitosan or a derivative thereof, preferably having a degree of deacetylation of about 30 to about 95%, preferably about 70 to about 90%, more preferably about 75 to about 85%, even more preferably about 80 to about 85%, and most preferably about 85%.

Advantageously, the molecular weight of the chitosan or the chitosan derivative of the gel composition or used to make the chitin or chitosan particles is of about 10 000 to about 500 000 D, preferably about 30 000 to about 100 000 D, more preferably about 50 000 to about 80 000 D.

According to an embodiment, the biomaterial includes in its composition about 0.1 to about 20%, preferably about 1 to about 20% w/w, more preferably about 1 to about 12% w/w, even more preferably about 1 to about 10%, most preferably about 1 to about 5% w/w of polysaccharide which is a chitosan or a chitosan derivative. In a specific embodiment, when the polysaccharide is a chitosan derivative, the composition of the biomaterial may include about 0.1 to about 20% of polysaccharide. According to a particularly preferred embodiment the chitosan derivative is succinochitosan glutamate.

According to an embodiment, the biomaterial used according to the invention comprises an injectable bioresorbable polysaccharide composition wherein the polysaccharide is succinochitosan glutamate. Advantageously, the succinochitosan glutamate has a degree of deacetylation of about 30 to about 95%, preferably about 70 to about 90%, more preferably about 75 to about 85%, even more preferably about 80 to about 85%, and most preferably about 85%. According to an embodiment, the succinochitosan glutamate has a molecular weight of about 10 000 to about 500 000 D, preferably about 30 000 to about 100 000 D, more preferably about 50 000 to about 80 000 D. According to an embodiment, the composition comprises about 0.1 to 20%, preferably 1 to 10%, more preferably 1 to 5% w/w succinochitosan glutamate by weight of the total composition. Advantageously, the biomaterial of the invention is a gel. The succinochitosan glutamate may be derived from chitosan of animal or vegetal origin. Advantageously, the succinochitosan glutamate used to manufacture the biomaterial of the invention is derived from GMP-grade chitosan.

In another preferred embodiment, the biomaterial is a chitosan or chitosan derivative gel including chitin particles.

According to a most preferred embodiment, the biomaterial to be used is a gel of succinochitosan glutamate, including chitin particles in suspension within the gel.

According to an embodiment, the chitosan used for manufacturing the biomaterial may be either of animal or vegetal origin. The use of a chitosan of animal origin, and more particularly crustaceans (prawn shells) or squids is of economic benefit. The use of a product of vegetal origin, and more particularly fungal, is generally better appreciated by consumers. Thus, according to a preferred embodiment, the chitosan used in the biomaterial of the invention, is extracted from fungi, such as for example Mucoralean strains, *Mucor racemosus* and *Cunninghamella elegans, Gongronella butleri, Aspergillus niger, Rhizopus oryzae, Lentinus edodes, Pleurotus sajo-caju*, more preferably *Agaricus bisporus*. According to another embodiment, the chitosan was produced from two yeasts, such as, for example *Zygosaccharomyces rouxii* and *Candida albicans*.

According to a particular embodiment, the particles included within the biomaterial to be used according to the invention contain or consist essentially of chitin and/or chitosan which are either of animal or vegetal origin. The particles may also be made of, or include, a mixture of chitin and chitosan. According to an embodiment, these particles may consist solely of chitin or solely of chitosan. According to an embodiment, the chitosan used to make the particles may have a degree of deacetylation of about 30 to about 95%, preferably about 70 to about 90%, more preferably about 75 to about 85%, even more preferably about 80 to about 85%, and most preferably about 85%. Advantageously, the chitosan used to make the particles may be of GMP grade. According to a preferred embodiment, the particles are of chitin obtained by reacetylation of a GMP grade chitosan. According to a preferred embodiment, the biomaterial is essentially free of endotoxins. According to another embodiment, the biomaterial includes deproteinized chitin particles essentially free of endotoxins.

According to an embodiment, the particles included within the biomaterial of the invention have a bioresorption time of 1 to 6 months. According to an embodiment, the chitin-only particles with a bioresorption time of 1 to 3 months, and chitosan-only particles have a bioresorption time of 1 to 4 months.

According to another embodiment, the amount of particles in the biomaterial of the invention may be of about 0.1 to 10% w/w, preferably of 1 to 5% w/w, more preferably of 1 to 2% w/w.

The amount of particles included within the biomaterial may depend on the final inventive application of the biomaterial and of the desired effect.

According to a preferred embodiment, the biomaterial is a chitosan or chitosan derivative gel, including 1 to 5% of chitosan particles or 1 to 5% of chitin particles. According to another embodiment, the biomaterial is a chitosan derivative gel, including 1 to 2% chitin particles. In a particularly preferred embodiment, the biomaterial is a gel consisting essentially of a chitosan derivative and water with chitin and/or chitosan particles suspended in the gel, where the gel is essentially free of any other formulation-enhancing agents such as plasticizers, surfactants, viscosity modifiers, and the like.

The biomaterial compositions used according to the invention may also include certain medicaments such as anesthetics, anti-inflammatories, analgesics, antimicrobials, antibiotics, growth factors, bone repair agents, and other actives and natural products to assist and provide further advantages in various applications, or may be formulated to exclude such additives.

According to another embodiment, the particles included within the biomaterial have a mean diameter of about to 150 μm, preferably 5 to 40 μm. According to an embodiment, the mean diameter of the particles are 3 to 12 μm, and preferably of 5 to 10 μm. According to another embodiment, the mean diameter of the particles are 10 to 32 μm. Preferably, the particles are microspheres.

Furthermore, these bioresorbable particles in suspension in the biomaterial should have a diameter such that the syringability of the product using 27G (or possibly 30G) needles remains satisfactory.

According to an embodiment, chitin and/or chitosan particles are obtained from chitin or chitosan crystals, having an average granulometry at the outset of 200 to 300 μm. The granulometry is reduced by any suitable technique known by one skilled in the art to lower the particle size of the particles, such as for example, but not limitatively, spray drying or micronization, optionally repeated more than once. These particles may then undergo a successive series of micronizations, while avoiding cryomicronization which sometimes damages the integrity of the micronized molecules. Subsequent sifting steps eliminate those particles which have a granulometry which is either too large or too small.

According to an embodiment, the particles of the biomaterial do not contain polymethacrylic acid and/or ester derivative thereof containing hydroxyl group, polyacrylamide, polymethacrylamide, poly-N-vinyl-2-pyrrolidone, polyvinyl alcohol.

According to another embodiment, the particles are not composite, but made of a single ingredient, which is preferably chitin.

According to an advantageous embodiment, the biomaterial has a pH which is compatible with dermatological and internal use, preferably a pH between 6.5 and 7.5, and ideally between 6.8 and 7.2.

According to another embodiment, the density of the biomaterial of the invention is comparable to that of the particles, preferably between 0.95 and 1.20, and ideally between 1.00 and 1.10.

The particles may be maintained in suspension by the viscosity of the particle-containing gel, the natural surfactant effect of chitin and chitosan, and also through the small size of the particles and the fact that their density is more or less equal to that of the gel. This homogeneity of density, the surfactant properties of chitin and chitosan and the small particle size ensures satisfactory homogeneity of the gel, avoiding clump formation which may block the fine needles, and avoiding the need for additional formulation-modifying agents such as plasticizers, surfactants, and viscosity modifiers.

The process for manufacturing a biomaterial to be used in the invention may involve steps in which chitosan or chitosan derivative with a degree of deacetylation of about 30 to about 95%, preferably about 70 to about 90%, more preferably about 75 to about 85%, even more preferably about 80 to about 85%, and most preferably about 85% is dissolved, followed by successive addition of glutamic acid and then succinic anhydrid, and neutralization. The addition of particles containing chitin and/or chitosan under agitation may be performed at various stages in the process, for example before or after addition of glutamic acid or at the end of the process.

During the neutralization step, the pH of this biomaterial is adjusted to somewhere between 6.5 and 7.5, ideally between 6.8 and 7.2, by addition of a base such as sodium hydroxide or triethanolamine.

The resulting biomaterial may not be affected by either pH or temperature. The latter is of particular interest as this means the product remains stable when stored at room temperature.

The process of manufacturing preferably also includes a sterilization step, such as a step involving irradiation or steam sterilization for example.

According to an embodiment, the chitin and the chitosan used for manufacturing the biomaterial of the invention and/or the particles are from one source, which is preferably GMP-grade chitosan. According to another embodiment, the manufacturing process of the chitin particles suspended in the biomaterial uses chitin obtained by reacetylation of a GMP-grade chitosan. The chitin used in the manufacturing process of the composition and/or of the particles is essentially free of protein.

The invention also relates to a medical device containing the said biomaterial for use in treating various conditions. According to a specific embodiment of the medical device, the said biomaterial is ready-to-use in a sterile syringe.

A subject of the invention is a method of treatment to fill a cavity in the human face or body, which may involve several successive injections of the said biomaterial, whereby each injection could be followed by massage of the surface of the skin over the injection area.

Another subject of the invention is the use of the said biomaterial for repair and/or treatment of vocal chord insufficiency or other bodily tissue such as cartilage, muscles, ligaments, tendons and/or corresponding post-operative regions as well as other conditions affecting tissue, bones and joints including, but not limited to, ailments due to age, arthritis, and areas of the body having insufficient soft tissue (e.g., tailbone, underside of the foot, etc.).

Biomaterial used according to the invention may be used in a method of treating and/or repairing the loss of fat pads under recurring pressure on the human body comprising administering a composition to the fat pads or surrounding tissue, wherein said composition is in the form of a gel comprising an injectable bioresorbable polysaccharide, and wherein said composition further comprises resorbable particles which are in suspension in said gel, the said particles comprising chitin and/or chitosan. In one embodiment, the fat pads are located at the soles of the feet, at the balls of the feet, at the heels of the feet, or at the coccyx.

Another subject is the use of the biomaterial as a filler for enhancement or enlargement of male or female genitalia.

The following are further examples of biomaterial which may be used in the invention. These examples are intended to illustrate possible biomaterials for use in the invention in a non-limiting manner:

EXAMPLE 1

Gel containing 4% of CHITOSAN (w/w)

Chitosan, GMP crustacean source, degree of deacetylation 85%, intrinsic viscosity of approx 150 cps (in a 1% acetic acid solution) was dissolved in purified water. Glutamic acid was added in stoicchiometric quantity (according to DDA) in the solution, which, after 15 to 20 minutes, produced chitosan glutamate. Succinic anhydride was then added (same quantity as glutamic acid) yielding a gel in the form of succino-chitosan glutamate. The pH of the gel was adjusted to 6,8-7,2 with sodium hydroxide. Gel was then filtered through a 160 μm filter to eliminate any possible undesired particle. Purified water was then added so as to obtain a 4% concentration of pure Chitosan in the gel. Gel obtained had a viscosity of approx 2500 cps, and was easy to inject through a 30 gauge needle. It was not sensitive to pH or temperature.

EXAMPLE 2

Gel containing 2% of CHITOSAN, in which 1% CHITIN microspheres (w/w) were in suspension A gel was prepared in the same way as in example 1, except for the concentration which was adjusted to 2% of pure CHITOSAN (w/w). Simultaneously, Chitosan was dissolved in a 1% acetic acid solution, and ethanol was added in a proportion of 30% of the final solution. A Büchi type spray-dryer was then used in order to obtain Chitosan microspheres, with a granulometry of 5 to 13 μm. These microspheres were poured into an acetic solution (stoicchiometric quantity of acetic acid calculated on DDA, so as to be able to reacetylate 25 to 30% of the polymer, so as to obtain more than 50% final acetylation). The resulting chitin microspheres were then incorporated into the gel so as to have 1% microspheres (w/w). The final colloidal suspension had a viscosity of approx 3500 cps, which made it easy to inject through a 27 gauge needle, and was not sensitive to pH or temperature.

EXAMPLE 3

Gel containing 5% of CHITOSAN, in which 1% CHITIN micronized particles (w/w) were in suspension A gel was prepared in the same way as in example 1, except for the concentration which was adjusted to 5% of pure CHITOSAN (w/w). Genuine CHITIN was obtained from the GMP Chitosan supplier. The granulometry of this powder was 200-300 μm. The powder was micronized and sieved so as to obtain a powder with a granulometry of 5 to 32 μm. Chitin particles were then incorporated into the gel so as to have 1% suspension in the gel. The final suspension had a viscosity of approx 4500 cps, and it was still possible to inject it through a 27 gauge needle. The final product was not sensitive to pH or temperature.

The invention claimed is:

1. A method of treating and/or repairing tissue post-operatively, comprising administering to tissue in need thereof a gel composition comprising an injectable bioresorbable succinochitosan glutamate and resorbable particles which are in suspension in said gel, said particles comprising chitin and/or chitosan.

2. The method according to claim 1, wherein the tissue comprises cartilage.

3. The method according to claim 1, wherein the composition induces fibrosis in the tissue.

4. The method according to claim 1, wherein the composition contains one or more medicaments selected from the group of: anesthetics, anti-inflammatories, analgesics, antimicrobials, antibiotics, growth factors or bone repair agents.

5. The method according to claim 1, wherein the succinochitosan glutamate has a degree of deacetylation of about 30 to about 95%.

6. The method according to claim 1, wherein the composition comprises about 0.1 to about 20% succinochitosan glutamate.

7. The method according to claim 1, wherein the weight percent of resorbable particles in the composition is between about 0.1% and about 10% by total weight of the composition.

8. The method according to claim 1, wherein the resorbable particles consist essentially of chitin.

9. A method of filling a cavity in a human face or body comprising administering to tissue surrounding said cavity a gel composition comprising an injectable bioresorbable succinochitosan glutamate and resorbable particles which are in suspension in said gel, said particles comprising chitin and/or chitosan.

10. The method according to claim 9, wherein the tissue comprises cartilage.

11. The method according to claim 9, wherein the composition induces fibrosis in the tissue.

12. The method according to claim 9, wherein the composition contains one or more medicaments selected from the group of: anesthetics, anti-inflammatories, analgesics, antimicrobials, antibiotics, growth factors or bone repair agents.

13. The method according to claim 9, wherein the succinochitosan glutamate has a degree of deacetylation of about 30 to about 95%.

14. The method according to claim 9, wherein the composition comprises about 0.1 to about 20% succinochitosan glutamate.

15. The method according to claim 9, wherein the weight percent of resorbable particles in the composition is between about 0.1% and about 10% by total weight of the composition.

16. The method according to claim 9, wherein the resorbable particles consist essentially of chitin.

* * * * *